(12) United States Patent
Wang et al.

(10) Patent No.: US 6,562,039 B1
(45) Date of Patent: May 13, 2003

(54) SPINAL FIXATION AND RETRIEVAL DEVICE

(76) Inventors: Chao-Jan Wang, 5F, 6, Chung-Yang Road, Tou-Fen Town, Miaoli Hsien (TW); Chung-Chun Yeh, 16, 1 Alley, Lane 65, Jen-Ai Road, Section 2, Taipei (TW)

( * ) Notice: Subject to any disclaimer, the term of this patent is extended or adjusted under 35 U.S.C. 154(b) by 164 days.

(21) Appl. No.: 09/644,209

(22) Filed: Aug. 23, 2000

(30) Foreign Application Priority Data

Dec. 10, 1999 (TW) ...................................... 088221109 U

(51) Int. Cl.⁷ ................................................. A61B 17/70
(52) U.S. Cl. .......................................... 606/61; 600/73
(58) Field of Search ........................... 411/411; 606/60, 606/61, 65, 73; 623/17.11, 17.16

(56) References Cited

U.S. PATENT DOCUMENTS

| | | | | |
|---|---|---|---|---|
| 5,042,982 A | * | 8/1991 | Harms et al. .................. | 606/61 |
| 5,067,955 A | * | 11/1991 | Cortel .......................... | 606/61 |
| 5,458,638 A | | 10/1995 | Kuslich et al. ................ | 623/17 |
| 5,658,285 A | * | 8/1997 | Marnay et al. ................ | 606/61 |
| 5,741,253 A | | 4/1998 | Michelson .................... | 606/61 |
| 5,984,927 A | * | 11/1999 | Wenstrom et al. ............ | 606/72 |
| 6,086,588 A | * | 7/2000 | Ameil et al. ................... | 606/60 |

FOREIGN PATENT DOCUMENTS

| | | |
|---|---|---|
| DE | 29712331 U | 10/1997 |
| FR | 2760355 A | 9/1998 |
| WO | WO 9525487 A | 9/1995 |
| WO | WO 95 32673 A | 12/1995 |

\* cited by examiner

*Primary Examiner*—Cary E. O'Connor
(74) *Attorney, Agent, or Firm*—Bacon & Thomas, PLLC

(57) ABSTRACT

A spinal fixation and retrieval device has a solid main body including a cone-like body at one end thereof and a column-like body connected to a base of the cone-like body. The cone-like body has a length which is less than one third of the length of the main body. The column-like body is provided with at least two threads which are separated from each other by a distance which is at least two times the width of the base of the threads.

8 Claims, 3 Drawing Sheets

SPINAL FIXATION AND RETRIEVAL DEVICE

FIELD OF THE INVENTION

The present invention relates to a spinal fixation and retrieval device.

BACKGROUND OF THE INVENTION

The conventional spinal disc spacer, for example, the RAMPS serial products made by AcroMed Corporation of the United States, is incapable of fusing with the vertebrae under treatment because the endplates of the vertebrae are not destroyed, and thus is apt to become disengaged with the two adjoining vertebrae. As a result, the conventional spinal disc spacer must be used in conjunction with an auxiliary device, such as a nail, a fixation rod, a fixation plate, etc. The use of such auxiliary device tends to inhibit the motion of the two adjoining vertebrae. Moreover, the auxiliary device does not prevent the spinal disc spacer from being disengaged with the vertebrae.

SUMMARY OF THE INVENTION

The primary objective of the present invention is to provide a spinal fixation and retrieval device free from the deficiencies of the conventional device described above.

In keeping with the principle of the present invention, the foregoing objective of the present invention is attained by the spinal fixation and retrieval device having an intervertebral disc main body formed of:

a cone-like body at one end; and a column-like body connected to a base of said cone-like body;

wherein said cone-like body has a length which is less than one third of a length of said intervertebral disc main body;

wherein said column-like body is provided with two or more threads or annular teeth having an interval thereof at least two times of a width of a base of said two or more threads or annular teeth.

DETAILED DESCRIPTION OF THE EMBODIMENTS

The spinal fixation and retrieval device of the present invention has a main body comprising a cone-like body and a column-like body at a base of said cone-like body. The cone-like body has a length which is less than one third of the total length of the main body. The column-like body is provided with two or more threads or annular teeth which are arranged at an interval not less than two times of a width of a base of the two or more threads or annular teeth.

The cone-like body is polygonally tapered or conical, preferably conical. The cone-like body has a round cross section at its base, and a flat top or point top. Preferably, the cone-like body has a dome shape.

The column-like body has a cross sectional profile corresponding to the profile of the cone-like body. The column-like body has a polygonal or round cross section, preferably round. The column-like body may be a regular cylindrical body having the same diameter or a modified cylindrical body having diameters which change smoothly from one end to another end thereof.

The cone-like body has a length, which is the vertical distance between the base and the top of the cone-like body, not exceeding one third of the total length of the main body of spinal fixation and retrieval device of the present invention. The length of the cone-like body is preferably between one fourth and one tenth of the total length of the device.

The column-like body has threads or annular teeth, which are preferably four in number. The ridge of the threads and annular teeth has a height ranging between 1 and 5 mm, preferably between 1.5 and 4.5 mm.

The threads and annular teeth are arranged at an interval which is preferably 3–10 times of the width of the base of the threads and annular teeth, and more preferably 4–8 times.

The main body of the device of the present invention is either solid or hollow and is made of a biomaterial, such as the stainless steel 316LVM, Ti6-4, cobalt-molybdenum-chromium alloy, etc. The main body may be provided with a tool hole to facilitate the implanting of the main body of the device.

The column-like body may be provided with a trench which is located between two of said two or more threads or annular teeth for enhancing the fixation effect. For the same reason, the column-like body may be provided at a tail end (an end which is away from said cone-like body) thereof with a trench.

The present invention is further described hereinafter by the following embodiments with reference to the accompanying drawings.

Figure 1A:
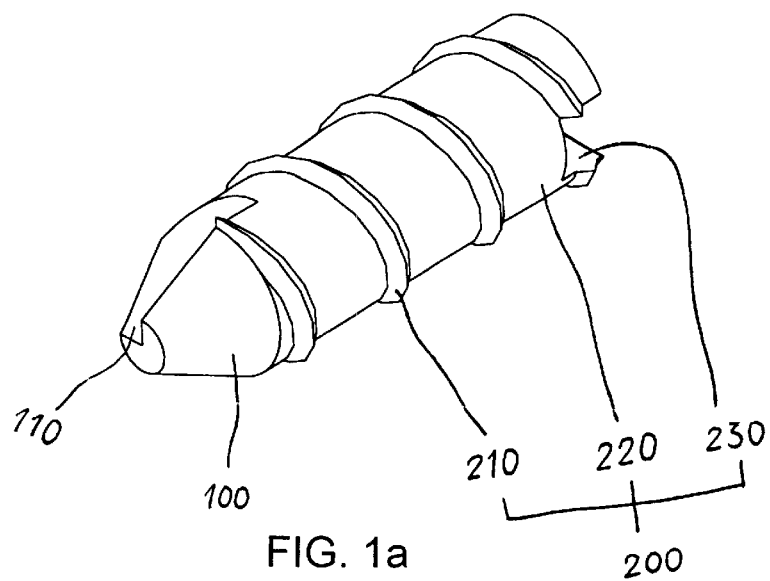
FIG. 1a is schematic views of a first preferred embodiment of the present invention.
Figure 1B:
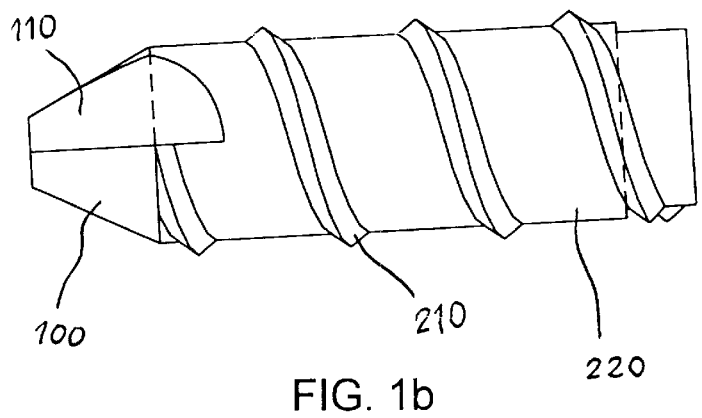
FIGS. 1b and 1c are a top plan view and a side plan view of the first preferred embodiment of the present invention shown in FIG. 1, respectively.
Figure 1C:
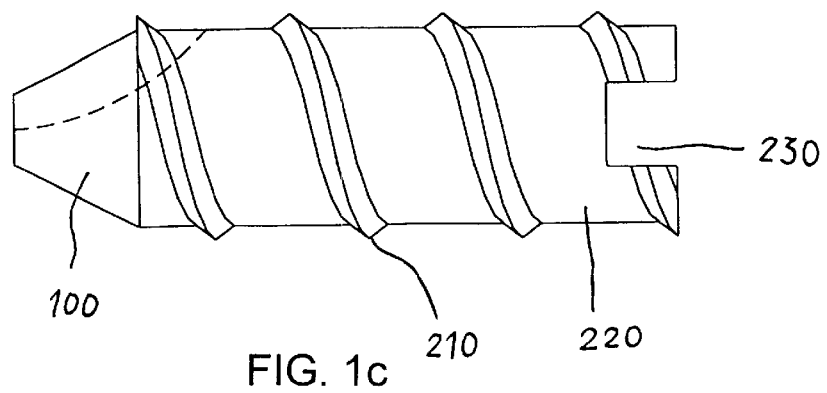

A first preferred embodiment of the present invention is shown in FIGS. 1a, 1b, and 1c, wherein a cone-like body 100 is provided in the implanting end thereof with a cut 110. A column-like body 200 is provided with four threads 210 which are separated by a distance 220 and a tool hole 230. The cone-like body 100 has a flat top. The column-like body 200 has a cylinder body.

Figure 2A:
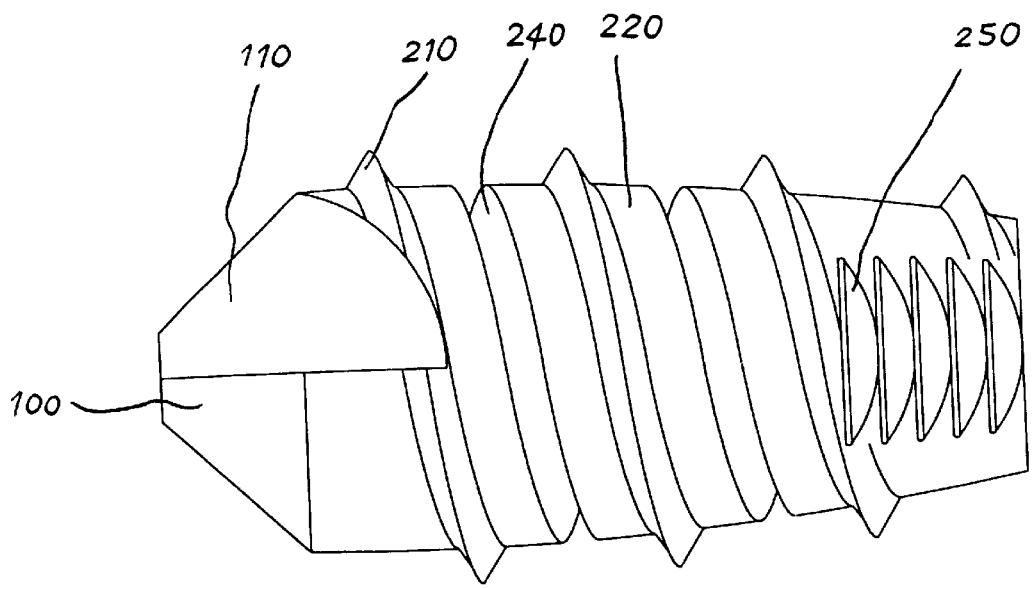
FIGS. 2a and 2b are a top plan view and a side plan view of a second preferred embodiment of the present invention, respectively.
Figure 2B:
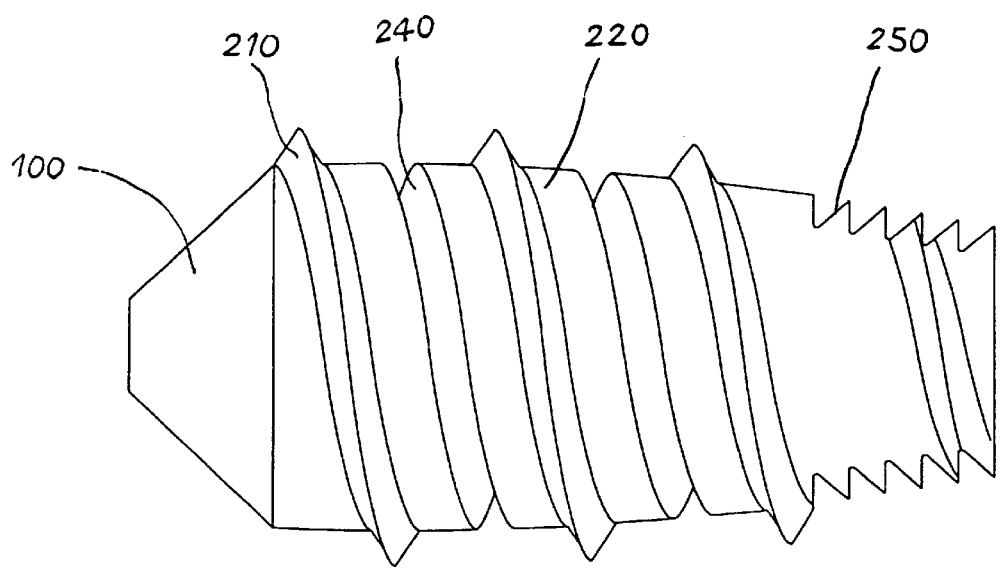

A second preferred embodiment of the present invention similar to that shown in FIGS. 1a–1c is shown in FIGS. 2a and 2b, wherein like elements and parts are designated by like reference numerals. As shown in FIGS. 2a and 2b, the column-like body has a large diameter at the end near the base of the cone-like body 100 compared to the tail end. The column-like body is provided with a trench 240 located between two threads 210 for reinforcing the fixation effect. The column-like body is further provided in the proximity of the tail end thereof with a plurality of grooves 250 for reinforcing the fixation effect.

Figure 3:
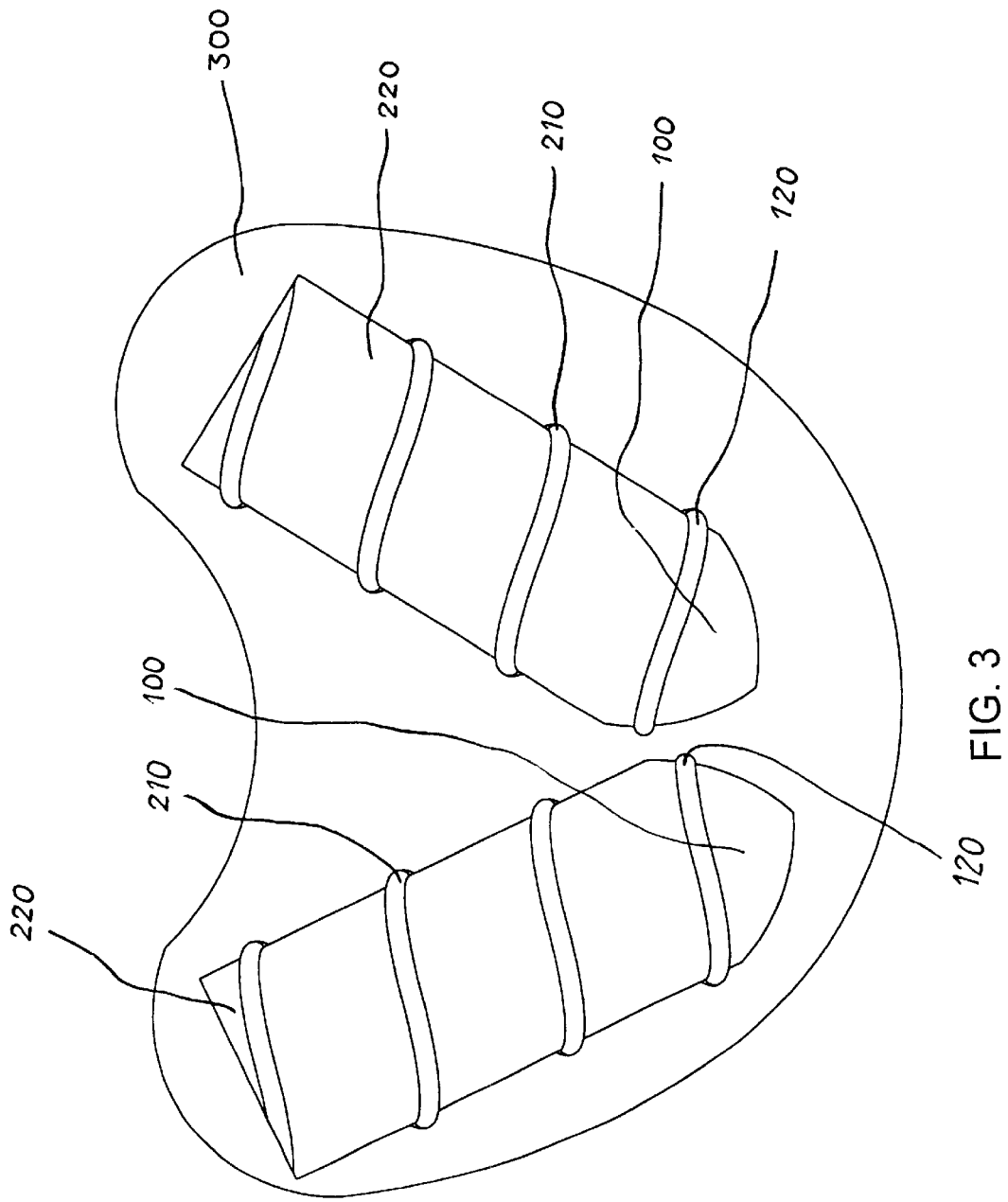
FIG. 3 shows a schematic view of a third preferred embodiment of the present invention which is implanted.

A third preferred embodiment of the present invention similar to that shown in FIGS. 1a–1c is shown in FIG. 3, wherein like elements and parts are designated by like reference numerals. The cone-like body 100 is provided with a thread 120 and has a dome shape, as shown in FIG. 3. The device of the present invention is implanted between end plates of two vertebrae, wherein only one vertebra 300 is shown.

What is claimed is:

1. A spinal fixation and retrieval device having an intervertebral disc main body formed of:
   a cone-like body at one end, the cone-like body having a flat top;
   a solid column-like body connected to a base of said cone-like body;
   wherein said cone-like body has a length which is less than one third of a length of said intervertebral disc main body;
   wherein said column-like body is provided with two or more threads or annular teeth having an interval thereof at least two times of a width of a base of said two or more threads or annular teeth;
   the disc main body adapted to be inserted between end plates of adjacent vertebrae; and
   wherein the column-like body has a larger diameter at the end near the base of the cone-like body than at the tail end thereof.

2. The device as defined in claim 1, wherein said intervertebral disc main body is substantially solid.

3. The device as defined in claim 1, wherein said cone-like body has a length which is in the range of one quarter to one tenth of a length of said intervertebral disc main body.

4. The device as defined in claim 3, wherein said two or more threads or annular teeth have an interval thereof which is 3–10 times of said width of said base of said two or more threads or annular teeth.

5. The device as defined in claim 4, wherein said two or more threads or annular teeth have an interval thereof which is 4–8 times of said width of said base of said two or more threads or annular teeth.

6. The device as defined in claim 1, wherein said two or more threads or annular teeth have an interval thereof which is 3–10 times of said width of said base of said two or more threads or annular teeth.

7. The device as defined in claim 6, wherein said two or more threads or annular teeth have an interval thereof which is 4–8 times of said width of said base of said two or more threads or annular teeth.

8. The device as defined in claim 1, wherein said column-like body is provided with a trench located between two of said two or more threads or annular teeth.

* * * * *